United States Patent [19]

Magnet

[11] Patent Number: 5,279,552
[45] Date of Patent: Jan. 18, 1994

[54] INTRADERMAL INJECTION DEVICE

[76] Inventor: Anton Magnet, 4364 Elder Ave., Seal Beach, Calif. 90740

[21] Appl. No.: 2,816

[22] Filed: Jan. 11, 1993

[51] Int. Cl.⁵ .............................................. B43K 5/00
[52] U.S. Cl. ........................................ 604/47; 74/57; 81/9.22
[58] Field of Search ................ 604/46, 47; 81/9.22; 74/57

[56] References Cited

U.S. PATENT DOCUMENTS

| | | | |
|---|---|---|---|
| 1,871,020 | 8/1932 | Wyzenbeek | 74/57 |
| 2,567,856 | 9/1951 | Polk | 74/57 |
| 2,588,623 | 3/1952 | Eliscu et al. | 604/47 |
| 2,840,076 | 6/1958 | Robbins | 128/253 |
| 3,509,786 | 5/1970 | Buttner | 81/9.22 |
| 4,204,438 | 5/1980 | Binaris et al. | 81/9.22 |
| 4,508,106 | 4/1985 | Angres . | |
| 4,644,952 | 2/1987 | Patipa et al. | 128/305 |
| 4,798,582 | 1/1989 | Sarath et al. | 604/47 |

FOREIGN PATENT DOCUMENTS

| | | | |
|---|---|---|---|
| 1587519 | 4/1981 | United Kingdom | 81/9.22 |
| 2234150 | 1/1991 | United Kingdom | 81/9.22 |

Primary Examiner—Paul J. Hirsch
Attorney, Agent, or Firm—Brown, Martin, Haller & McClain

[57] ABSTRACT

An intradermal injection device is described which is placed against the skin of a patient and uses a reciprocating needle to inject ink, dye or similar fluid under the patient's skin, usually in a predetermined visible pattern. Unlike prior art devices of this type, however, the present device is readily disassembleable for rapid and thorough cleaning, since it is formed of a plurality of components which fit together through easily separable and cleanable couplings such as overlapping sealed (O-ring interference) fits or by threads. It also has a unique structure which avoids potential contamination of the drive components by having the drive mechanism offset at a substantial angle from the axis of the reciprocating needle and needle drive shaft and also by preferentially including internal fluid passage barriers such as fluid knock-out spaces. The device is preferably formed of metal such as aluminum or stainless steel, and may be electrically or fluid driven.

11 Claims, 2 Drawing Sheets

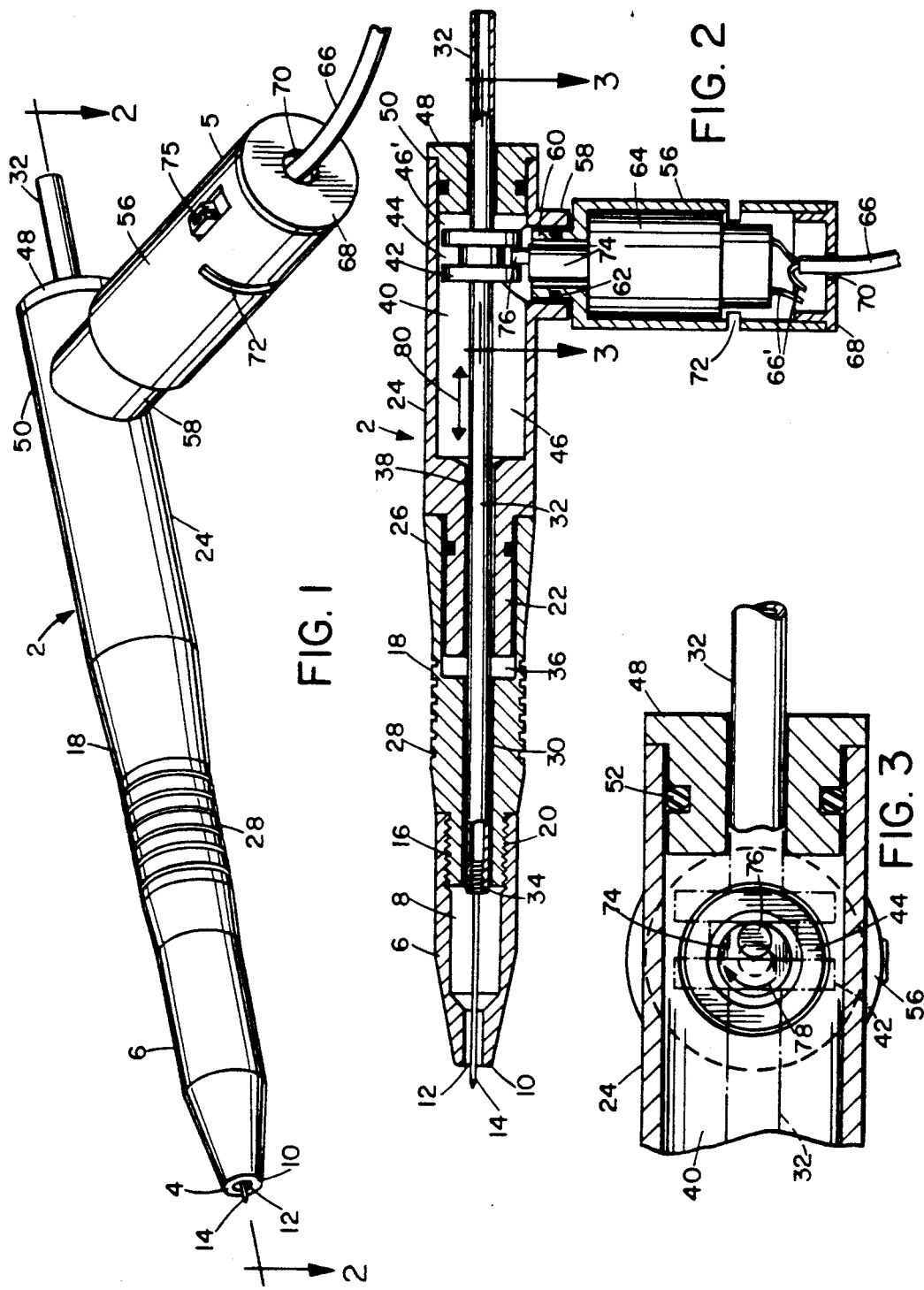

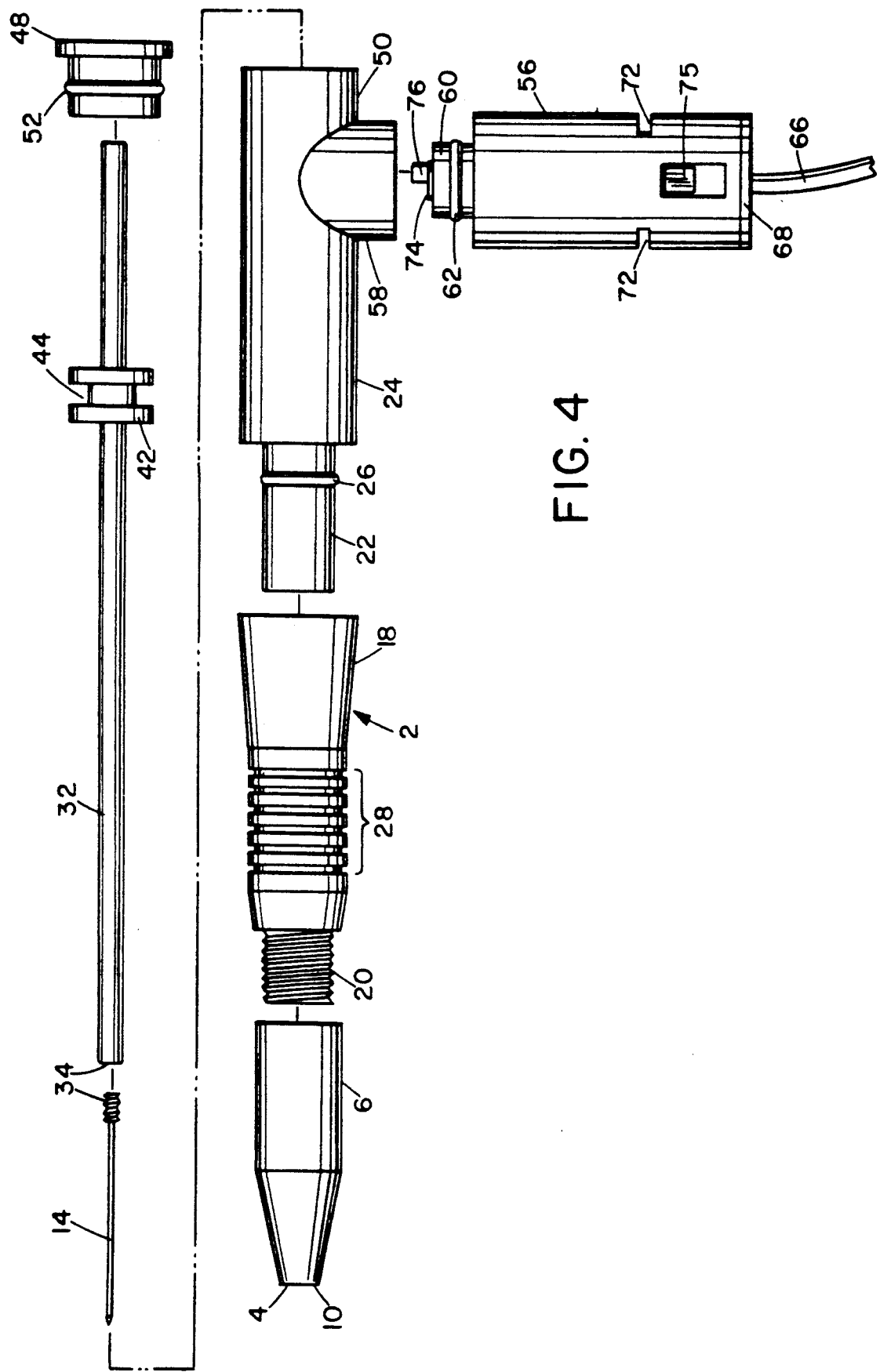

INTRADERMAL INJECTION DEVICE

BACKGROUND OF THE INVENTION

1. Field of the Invention

The invention herein relates to intradermal injection devices, sometimes referred to as tattooing devices.

2. Description of the Prior Art

There have been intradermal injection or surgical devices for many years. They are commonly used to create decorative tattoos on a person's skin or to form permanent eyelid liners to replace paint-on cosmetic eyelid liners. The devices inject ink, dye or other marking fluid (referred to hereafter collectively as "ink" for brevity) just under the skin surface, so that the ink is retained within the skin and the color of the ink and the design formed by the ink injection pattern is visible.

The devices normally comprise a skin-penetrating needle which has the capacity to retain some quantity of ink or dye, a mechanism to reciprocate the needle for repeated punctures of the skin to implant the ink under the skin in the desired pattern, and a pen-like housing for the device which the operator holds and uses to guide the device. There are also some sort of off-on switch and power source for the reciprocating drive mechanism. With some devices the operator repeatedly dips the needle into an ink pool to coat the needle, while other devices have built-in reservoirs for the ink from which the ink is fed continuous to the needle.

A number of different devices, particularly with different types of reciprocating needle drives, have been disclosed over the years, and many of them have become commercial products. Typical of well-known devices are those described in U.S. Pat. Nos. 2,840,076 (Robbins: 1976); 4,508,106 (Angres: 1985); 4,644,952 (Patipa et al.: 1987) and 4,798,582 (Sarath et al.: 1989).

All of these devices have one or more disadvantages, however. One of the most significant is their inability to be readily and easily cleaned after use. While cleaning has always been recognized as important, in the past it was not uncommon for some operators to perform relatively low-level cleaning between consecutive uses, with full and thorough cleaning performed only periodically, such as overnight. This was because thorough cleaning required complex and time-consuming disassembly, including removal and retention of small parts, and/or lengthy immersion of the device in cleaning solvents such as acetone or in ultrasonic cleaning devices. Alternatively, a practitioner would have a number of devices, and would use each one only once before disassembling it for a thorough cleaning. Commonly the used devices were collected during the day and then at the end of the day all were disassembled and subjected to overnight cleaning.

Past devices also were structured so that some parts could only be cleaned with difficulty, particularly the drive mechanism. In the prior art devices the drive mechanism was in a direct line with the needle, and the rapid reciprocation of the needle would cause ink, sweat and skin fluids to be drawn into the drive mechanism, from which they could be removed only with great difficulty. Autoclaving was not feasible, because of the thermal degradation of the electrical components of the drive mechanism and the fact that an autoclave sterilizes but does not clean objects, so the time-consuming and difficult disassembly and subsequent ultrasonic or solvent cleaning was normally required.

Contaminated ink pools and ink residue within the devices also posed cleaning problems. Because disassembly was difficult and often incomplete prior to cleaning, inks and ink residues could accumulate in cavities within the device and serve as sources of contamination and disease.

Transmittal of diseases from one patient to another has always been the most important concern about use of the intradermal injection devices. In the past various infections of the skin could be transmitted. Serious as these were, however, they were normally curable if treated promptly. More recently, however, the appearance of the AIDS virus and its tendency to be transmitted primarily through openings and lesions in the skin or other bodily surfaces have transformed the context in which intradermal injection devices are used. Now transmittal of the infectious AIDS virus will result not just in an illness or minor skin infection, but rather with the inevitable death of the infected person. No longer can devices of the prior art type, with their inability to be easily and thoroughly cleaned after even a single use, be tolerated.

In order to accomplish this, however, it will be necessary to make fundamental changes in the basic design of such devices, such that a unit can be readily disassembled, quickly and thoroughly cleaned, and readily reassembled. It is to this end that the present invention is directed.

SUMMARY OF THE INVENTION

The invention herein is an intradermal injection device (or tattooing device or intradermal surgical device) which is placed against the skin of a patient and uses a reciprocating needle to inject ink, dye or similar fluid under the patient's skin, usually in a predetermined visible pattern. Unlike prior art devices of this type, however, the present device is readily disassembleable for rapid and thorough cleaning, since it is formed of a plurality of components which fit together through easily separable and cleanable couplings such as overlapping sealed (O-ring interference) fits or by threads. It also has a unique structure which avoids potential contamination of the drive components by having the drive mechanism offset at a substantial angle from the axis of the reciprocating needle and needle drive shaft and also by preferentially including internal fluid passage barriers such as a fluid knock-out space.

The device is preferably formed of metal such as aluminum or stainless steel, and may be electrically or fluid driven.

In its broadest form, the invention is an intradermal injection device for injecting fluid under the skin of a patient, the device being easily disassemble-able and readily cleanable, and comprising: an elongated body having distal and proximal ends; a shaft hole extending coaxially through the body; a drive shaft removably disposed for reciprocal motion within the shaft hole, and extending outwardly therefrom at least at the proximal end, the outward extension of the shaft having a cam follower mounted thereon; a cam removably engaging the cam follower to drive the cam follower in a reciprocating path co-axial of the body; a drive mechanism for the cam, the drive mechanism being at an angle to the axis of the shaft and body and removable from the body; and a needle removably mounted on the distal end of the drive shaft and extending through the reservoir and outwardly through the access hole, the needle being adapted carry to a quantity of the fluid on the surface thereof; whereby upon reciprocation of the drive shaft by the cam the needle is caused to reciprocate and inject the carried fluid under the skin of a patient whose skin is in contact with the distal end of the device; and whereby upon completion of the injection the needle, drive shaft, drive mechanism and body can all be readily and rapidly separated from one another for expedient and thorough cleaning.

BRIEF DESCRIPTION OF THE DRAWINGS

FIG. 1 is a perspective view of a complete unit of one embodiment of the device of this invention;

FIG. 2 is a sectional view taken on Line 2—2 of FIG. 1;

FIG. 3 is an enlarge sectional view taken on Line 3—3 of FIG. 2; and

FIG. 4 is an exploded side elevation view showing all of the components of the device separated for cleaning.

DETAILED DESCRIPTION AND PREFERRED EMBODIMENTS

The device of this invention overcomes the difficulties of the prior art devices by incorporating a structure which is readily disassembleable for cleaning and which removes key components from contact with potentially contaminated fluids, both inks and bodily fluids. Heretofore few devices had even one of these characteristics, and most had neither.

The device of this invention and its operation are most easily understood by reference to the drawings. The overall device 2 is best illustrated in FIGS. 1 and 4. Starting from the distal or patient-contact end 4 of the device 2, there is first a tip section 6 which has an internal chamber 8. A portion of the tip section 6 tapers toward a small tip 10 at the distal end 4 to enable the operator to follow the desired pattern more easily. The tapered end 10 has a hole 12 coaxial with the main part of the device and forming a passage from the outside of the device into the chamber 8, through which the distal end of the needle 14 passes. The proximal end of the tip section 6 has threads 16 to enable it to be joined to the next component, barrel 18.

It is possible that chamber 8 could serve as a reservoir in which a small supply of ink (not shown) is retained, for transfer to the needle 14. However, because of the tendency of inks to dry within the device, especially in the enclosed shaft or needle passages, in practice chamber 8 will find little use as a reservoir. More preferably, ink is transferred to the needle 14 by dipping the needle into a small separate external container of ink (not shown) so that the ink is adsorbed onto the surface of the needle 14. Chamber 8 then serves as a "knock-out" chamber to prevent any ink or bodily fluid which migrates up the needle 14 or is carried up through hole 12 by needle reciprocation or capillary action from passing any further into the device. The volume of the chamber 8 is not critical, as long as it is of significantly greater volume than capillary size, and will normally be on the order of about 1-2 milliliters. Smaller volumes may be used, but larger volumes are less desirable, since they enlarge the outer dimensions of the tip section 6 and make it more difficult to manipulate.

Barrel 18 is generally cylindrical, and is threaded at its distal end with threads 20 which mate with threads 16 of reservoir 6 to form a fluid impervious barrier. At its proximal end barrel 18 is hollow and forms an overlapping sealing fit with a coaxial extension 22 of reciprocation unit 24. A fluid-tight seal is formed by at least one O-ring 26. The outer surface of barrel 18 may be knurled or grooved as at 28 to provide for more secure gripping by the operator. The exact form, length and dimensions of the tapers shown in the illustrated preferred embodiment are not critical, and can be varied to suit the size and exact shape of each variation of the device.

Barrel 18 also has a coaxial hole 30 penetrating completely through it, through which drive shaft 32 passes to connect to needle 14 through threaded joint 34. At the proximal end of hole 30 is a second "knock-out" space 36. This is a further safeguard to prevent ink or bodily fluid which gets past chamber 8 (or is in chamber 8, if chamber 8 is used as a reservoir) from passing on through hole 38 into the reciprocation chamber 40 and from there to the drive mechanism. Alternatively one could install a gasket surrounding shaft 32 at the proximal end of hole 30, but the gasket material would have to be selected such that it could sustain the constant flexing resulting from reciprocation of shaft 32 without degradation or loss of sealing function.

The reciprocation mechanism is housed in reciprocation unit 24. Unit 24 has an interior hollow chamber 40 through which drive shaft 32 passes. The extension 22 of unit 24 also has a coaxial hole 38 through which the shaft 32 continues as illustrated. Near the distal end of shaft 32 is cam block 42, which has a peripheral groove 44 which serves as the cam follower. Cam block 42 can be formed integrally with the shaft 32 or can be formed separately and then fixedly joined to shaft 32. The interior volume of the chamber 40 is sufficiently large to permit cam block 32 to reciprocate axially of the chamber 40. Additional volume of chamber 40 is desirable, as shown at 46 and 46', to lighten the device 2 and to facilitate removal of shaft 32 as described below.

The proximal end 50 of device 2 is closed by plug 48, which forms an overlapping sealing fit secured by O-ring 52. Plug 48 also has a coaxial hole 54 therethrough, to which the proximal end of shaft 32 protrudes. Hole 54 serves as an alignment bearing to maintain the coaxial alignment of shaft 32, in cooperation with hole 30 and to a lesser extent hole 38. Holes 12, 30, 38 and 54 also serve as air vents to allow the entire device to be assembled in a liquid-tight configuration without causing pressure build-up.

The drive mechanism is contained in housing 56, which is disposed perpendicularly to the main axis of the device 2 and shaft 32. The unit 24 has formed therein a perpendicular extension 58 into which a neck 60 formed at the inward end of housing 56 fits, where it is retained by O-ring 62.

Within housing 56 is rotary motor 64, here illustrated as a conventional electric motor. It could, however, be any other type of small rotary motor. Those skilled in the art will be familiar with the various motors commercially available and will be readily able to select from any of a number of quite suitable versions. Motor 64 receives electric power through wire pair 66, which will be plugged into a conventional electrical outlet (not shown). The outer end of housing 56 is closed by cap 68, through which wire pair 66 passes via hole 70. Hole 70 may be sealed by an elastic grommet (not shown) if desired. Vent slots 72 are formed in housing 56 to provide pressure relief when cap 68 closes the end of housing 56.

There will also be means to stop and start motor 64. In the illustrated embodiment this is shown as slide switch 75 mounted in the housing 56 and connecting the ends 66, of one of the wires in pair 66. Alternately switch 75 could be an in-line switch mounted externally of the device 2 somewhere along wire pair 66, or a floor mounted switch controlled by the operator's foot, and into which wire pair 66 is plugged.

At the inward end of motor shaft 74 is eccentrically mounted cam 76. Cam 76 extends into groove 44 in cam block 42. As motor shaft 74 turns, cam 76 rotates in a circular path as indicated by arrow 78 in FIG. 3. Groove 44, acting as a cam follower, reciprocates axially within chamber 40, simultaneously reciprocating shaft 32 and connected needle 14 as indicated by double-headed arrow 80. As needle 14 reciprocates, it alternately moves into chamber 8 and picks up ink and then moves outwardly with the ink, punctures the patient's skin, and deposits the ink under the skin surface. Thus with each reciprocation, a quantity of ink is picked up on that portion of the surface of needle 14 which comes within the chamber 8. The surface of needle 14 is essentially completely covered with ink, and the reciprocation causes a continual flow of ink distally along the needle 14 and into the patient's skin.

It will be recognized that while an electric drive motor which plugs into a conventional outlet is preferred and is the simplest embodiment, one could also have other forms of drive mechanisms. One such could be a fluid drive motor, such as an air- or gas-driven motor, which would be operated by air or gas under pressure from a supply such as a portable air tank or fixed air pipe. This type of embodiment could be preferred where, for instance, consistent electric power sources are not available or where there is a hazard from a spark or short circuit. One might also use a water drive motor.

The ready facility of this device to be cleaned, and the ability of its structure to prevent penetration of much of the operation portion of the device by ink or bodily fluids is evident from the drawings, particularly FIG. 4. Tip section 6 is easily unscrewed from barrel 18 for emptying of residual ink or bodily fluid which has passed into chamber 8 and flushing out with a cleaner/disinfectant liquid. If chamber 8 is used as a reservoir, it can then be refilled with fresh ink from an uncontaminated supply. The remaining components - barrel 18, unit 24, housing 56 and caps 48 and 68, all disassemble by merely being pulled apart. Removal of housing 56 from extension 58 simultaneously removes cam 76 from groove 44, so that shaft 32 can be moved distally, for unthreading from needle 14. Needle 14 can then be removed for cleaning, while shaft 32 is withdrawn through the proximal end of the device after removal of cap 48. Disassembly and thorough cleaning of the improved device of the present invention are therefore much simpler, quicker and more efficient than has been possible with the prior art devices.

It will be seen that because of its offset location, the presence of the knock-out spaces 8 and 36, and the expanded shape of cam block 42, the drive mechanism within housing 56 cannot come into contact with ink or bodily fluids. Consequently the problems of prior art devices with in-line drive mechanisms relating to contamination of the drive mechanisms and the subsequently difficulty in cleaning those mechanisms, simply do not occur in the improved device of the present invention.

The device of the present invention may be made of any suitable material or combination of materials which will be structurally sound, resistant to inks and bodily fluids and substantially non-porous. Preferably the principal components will be made of metal, such as aluminum or stainless steel, while the O-rings will be made of medically acceptable elastomers. Portions of the device may also be made of engineering plastics in some cases, but the drive shaft 32 and especially the needle 14 will essentially always be made of metal.

It will be evident that there are numerous embodiments of the device which, while not expressly described above, are clearly within the scope and spirit of the invention. The above description is therefore intended to be exemplary only, and the actual scope of the invention is to be determined solely from the appended claims.

I claim:

1. An intradermal injection device for injecting fluid under the skin of a patient, said device being easily disassemble-able and readily cleanable, and comprising:
   an elongated body having distal and proximal ends;
   a shaft hole extending coaxially through said body;
   a drive shaft removably disposed for reciprocal motion within said shaft hole, and extending outwardly therefrom at least at said proximal end, the outward extension of said shaft having a cam follower mounted thereon;
   a cam removably engaging said cam follower to drive said cam follower in a reciprocating path co-axial of said body;
   a drive mechanism for said cam, said drive mechanism being at an angle to said axis of said shaft and body and removable from said body;
   a hollow fluid reservoir for said fluid removably attached to the distal end of said body in a fluid-tight manner, said reservoir having an access hole to the outside thereof aligned co-axially of said shaft hole; and
   a needle removably mounted on the distal end of said drive shaft and extending through said reservoir and outwardly through said access hole, said needle being adapted carry to a quantity of said fluid on a surface thereof;
   whereby upon reciprocation of said drive shaft by said cam said needle is caused to reciprocate and inject said carried fluid under the skin of a patient whose skin is in contact with the distal end of said device; and
   whereby upon completion of said injection said needle, drive shaft, drive mechanism and body can all be readily and rapidly separated from one another for expedient and thorough cleaning.

2. An intradermal injection device as in claim 1 further comprising means to retain the proximal end of said shaft in co-axial alignment.

3. An intradermal injection device as in claim 1 wherein said drive mechanism is aligned substantially perpendicular to said axis of said shaft and said body.

4. An intradermal injection device as in claim 1 wherein said drive mechanism comprises a motor with a rotary shaft.

5. An intradermal injection device as in claim 4 wherein said cam comprises an eccentrically mounted extension of said rotary shaft, and said cam follower comprised a collar on said drive shaft and having a peripheral groove into which said cam extends.

6. An intradermal injection device as in claim 4 wherein said motor is electrically driven.

7. An intradermal injection device as in claim 4 wherein said motor is fluid driven.

8. An intradermal injection device as in claim 1 wherein said body is formed of a plurality of coaxial sections removably joined together in a fluid-tight manner.

9. An intradermal injection device as in claim 8 wherein there is an enclosed space between the adjacent ends of adjacent sections, said space serving to prevent fluid transfer between said sections.

10. An intradermal injection device as in claim 8 wherein said fluid-tight manner of joining at least one said coaxial section is an overlapping sealing arrangement with an adjacent section.

11. An intradermal injection device as in claim 10 wherein each said overlapping sealing arrangement includes an O-ring.

* * * * *